United States Patent [19]
Storz

[11] Patent Number: 6,039,687
[45] Date of Patent: Mar. 21, 2000

[54] RECTOSCOPE WITH SEMI-REFLECTIVE TUBE SURFACE

[75] Inventor: Karl Storz, deceased, late of Tuttlingen, Germany, by Sybill Storz-Reling, executrix

[73] Assignee: Karl Storz GmbH & Co. KG, Germany

[21] Appl. No.: 09/051,836

[22] PCT Filed: Oct. 18, 1996

[86] PCT No.: PCT/DE96/01989

§ 371 Date: Jul. 13, 1998

§ 102(e) Date: Jul. 13, 1998

[87] PCT Pub. No.: WO97/14287

PCT Pub. Date: Apr. 24, 1997

[30] Foreign Application Priority Data

Oct. 19, 1995 [DE] Germany .............. 295 16 561

[51] Int. Cl.[7] ....................................... A61B 1/06
[52] U.S. Cl. .......................................... 600/135
[58] Field of Search ................... 600/103, 105, 600/114, 127, 134, 135, 138, 167, 178, 182, 199, 200, 160

[56] References Cited

U.S. PATENT DOCUMENTS

| 738,887 | 9/1903 | Zeng ..................... 600/178 |
| 760,395 | 5/1904 | Houghton ............... 600/200 |
| 799,114 | 9/1905 | Tracey ................... 600/127 |
| 1,624,716 | 4/1927 | Cerbo .................... 600/135 |
| 2,823,666 | 2/1958 | Hallpike et al. ......... 600/200 |
| 3,481,325 | 12/1969 | Glassman ............... 600/179 |
| 3,889,661 | 6/1975 | Fiore . | |
| 4,306,546 | 12/1981 | Heine et al. . | |

FOREIGN PATENT DOCUMENTS

| 979425 | 4/1951 | France . |
| 203784 | 9/1923 | United Kingdom . |

Primary Examiner—John P. Leubecker
Attorney, Agent, or Firm—St. Onge Steward Johnston & Reens LLC

[57] ABSTRACT

A rectoscope for examination of the rectum includes a wide-lumen tube, a light conductor connection coupling light from an illumination device to the wide-lumen tube, and a viewing optic disposed in the proximal region of the wide-lumen tube and focused on the center region of the distal opening. Substantially the entire internal side of the wide-lumen tube includes a semi-reflecting surface such that the internal side conducts light from the light conductor connection to the distal opening.

12 Claims, 1 Drawing Sheet

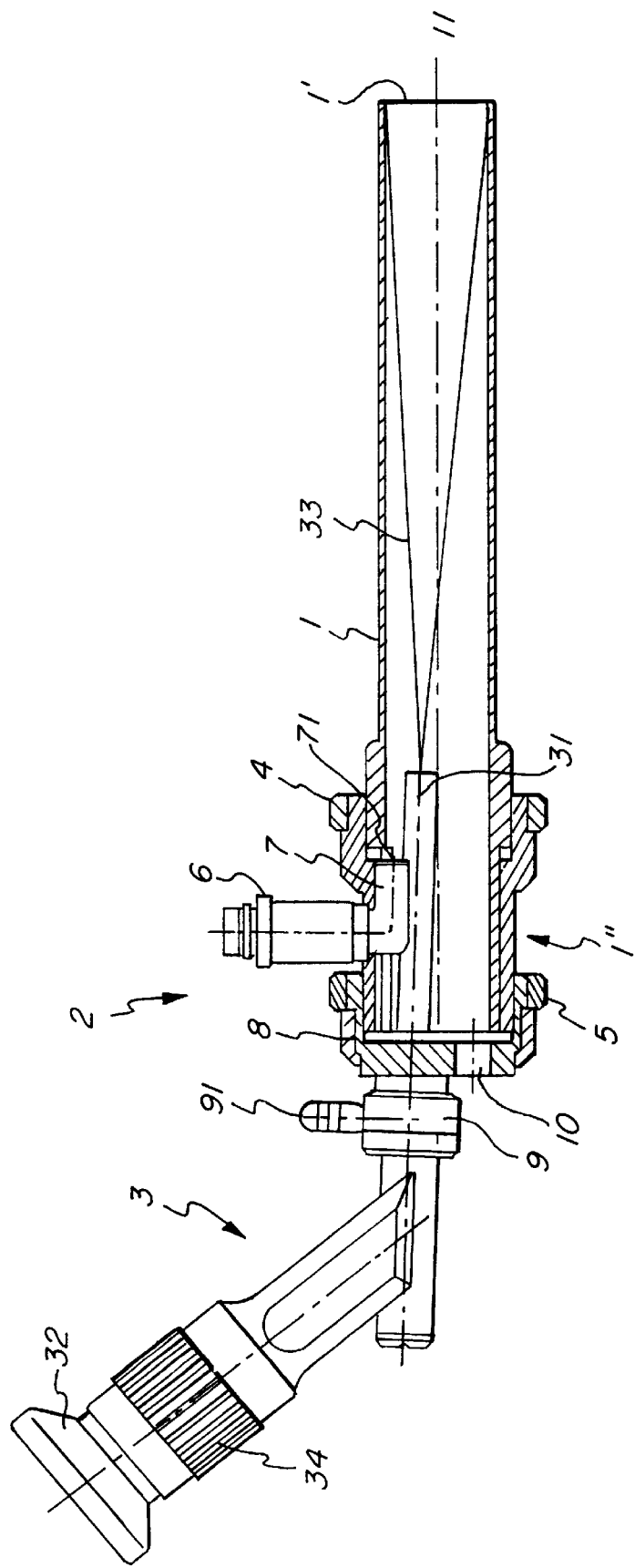

RECTOSCOPE WITH SEMI-REFLECTIVE TUBE SURFACE

DESCRIPTION

1. Technical Field

The present invention relates to a rectoscope for, in particular, the examination of the rectum according to the generic part of claim 1.

2. State of the Art

Generic type rectoscopes, manufactured by way of illustration by Karl Storz GmbH & Co, KG, Tuttlingen, Germany, have a wide-lumen tube the distal end of which can be inserted, for instance, into the rectum.

Furthermore, an illumination device is provided, the light of which is coupled proximally or distally into the wide-lumen tube. The examining person views the to-be-examined area of the rectum through the open proximal end of the wide-lumen end without any additional auxiliary viewing devices, such as a microscope or the like.

Therefore, the known generic type rectoscopes have the disadvantage that viewing of the to-be-examined area of the rectum occurs with the naked eye. Thus, the examining person is unprotected, for instance, against splattering blood. More important, however, viewing does not deliver a high-contrast image, in particular, if the examining person wears eyeglasses, due to the interference of reflections of the illumination light from the inside wall of the wide-lumen tube.

DESCRIPTION OF THE INVENTION

The object of the present invention is to further develop a rectoscope according to the generic part of claim 1 in such a manner that a high-contrast image of the to-be-examined area is obtained obviating the use of a distal optic which can easily soil and, moreover, takes up a part of the distal tube lumen so that it cannot be utilized for instruments.

A solution to this object according to the present invention is set forth in claim 1. Further embodiments of the present invention are the subject matter of claims 2 and the following claims.

An element of the present invention is that a viewing optic, which can be focused on the central region of the distal opening of the tube, is attached at the proximal end of the wide-lumen tube. This viewing optic, the focus plane of which lies in the region of the distal opening, yields a high-contrast image, because due to the focusing of the opening, the reflections of the illumination light from the semi-reflecting inside wall of the tube no longer interfere. It is especially advantageous if the enlargement of the viewing optic is selected in such a manner that the viewer only sees the distal opening and, if need be, a small part of the distal end of the tube.

In a preferred embodiment of the present invention the focus plane of the viewing optic is adjustable. In this way, the regions outside the plane in which the distal opening of the rectoscope is located can also be viewed sharply.

In principle, any optics can be employed as the viewing optics as long as they permit, with a terminal window of the viewing optic disposed in the region of the proximal end of the rectoscope, observation respectively viewing of the distal end of the rectoscope.

However, it is especially advantageous if the observation optic is an endoscope, the length of which is dimensioned in such a manner that it projects only partly into the wide-lumen tube so that the endoscope lens (still) is disposed in the proximal region. Thus the viewing optic can be constructed in a simpler and therefore more economical manner of endoscope components already available for other purposes.

Furthermore, the beam path can be bent in a simple manner in such a way that the eyepiece forming an angle with the axis of the tube does not hinder free access to the proximal end of the rectoscope.

Free access to the proximal end is further facilitated by the viewing optic being disposed eccentric in relation to the wide-lumen tube.

In particular, the viewing optic can be attached via a standard coupling to a flange which is provided with at least one instrument. Due to the fact that both the viewing optic and the illumination device are located in the proximal region of the wide-lumen tube, this instrument can be moved unhindered over the entire region of the distal opening of the tube and can simultaneously be viewed with the viewing optic.

In order to avoid reflections it is also advantageous if the axes of the illumination device and the viewing optic form an angle < > °.

BRIEF DESCRIPTION OF THE DRAWING

The present invention is made more apparent by way of example in the following without the intention of limiting the scope or spirit of the overall inventive idea using a preferred embodiment with reference to the drawing, FIG. 1 shows a cross section of the invented rectoscope.

DESCRIPTION OF THE PREFERRED EMBODIMENT

The rectoscope, which is especially suited for the examination of the rectum, shown in FIG. 1 is provided with a wide-lumen tube 1 which is open at its distal end 1' thus at the front. The rectoscope is inserted with its distal end 1', by way of illustration, into the rectum.

An element of the present invention is that an illumination device 2 and a viewing optic 3 are disposed in the region of the proximal end 1" of the wide-lumen tube 1.

For this purpose, two couplings 4 respectively 5 are provided on the tube 1, of which coupling 4 permits a detachable connection of the illumination device 2 and coupling 5 permits the detachable connection of the viewing optic 3 to the tube 1.

The illumination device 2 is provided with a light conductor connection 6 and a light conductor element 7, which projects through an opening in the tube into the interior of tube 1.

The light conductor connection 6, which may be constructed in the same manner as known endoscopes, by way of illustration from Karl Storz GmbH & Co., is located outside tube 1 and permits coupling in the light of a not depicted illumination light source via an also not depicted light conductor cable. The connection of a conventional illumination light source via a light conductor cable to the light conductor connection 6 is known, therefore obviating closer description here.

Light conductor element 7 conducts the light coupled into the light conductor connection 6 to its light exit surface 71 in the tube. Light exit area 71 is preferably located, like in the shown preferred embodiment, in the region of the proximal end 1" of tube 1. The light emerging from the light exit area 71 of the light conductor element 7 is coupled into the wide-lumen tube.

In the shown preferred embodiment the part of the light conductor element 7 projecting into the interior of tube 1 is not disposed in the tube axis 11. The internal side of tube 1 is designed semi-reflecting so that the internal side of the tube serves as a light transmitter for the light emerging from the light exit area 71. In this way the light emerging from the light exit area 71 illuminates, if need be after reflection from the inside wall of tube 1, the distal terminal area 1' as well as the region of the interior of the body adjacent thereto.

Furthermore, the illumination device 2 may be provided at its light entry or its light exit with an optical system (not depicted in the drawing), which permits focusing respectively altering the angle of the opening of the light cone emerging from the light exit area 71 so that the size of the illuminated area of the body can be varied.

In the shown preferred embodiment, a flange 8 is provided which covers the proximal opening of tube 1 like a kind of cover and which is detachably connected to the tube by means of a coupling 5. The flange 8 bears a coupling 9 which is designed as a conventional endoscope coupling as they are provided, by way of illustration, on trocar shafts for connecting endoscopes. 91 stands for a lever for operating coupling 9.

An endoscope, which serves as the viewing optic 3, is connected by means of the coupling 9 to the flange 8. In the shown preferred embodiment, the endoscope 3 is provided with a rod-shaped component 31 and an eyepiece component 32, which is set at an angle to the rod-shaped component 31 for better accessibility and for easier handling.

The length of the rod-shaped component 31 is dimensioned in such a manner that it partly projects into tube 1. The endoscope lens, not depicted in the drawing, has an opening angle 33, which is selected in such a manner that the distal terminal area 1' of tube 1 is completely imaged.

The image of the endoscope lens is transmitted in an as such known manner by means of an image transmitter, which may be provided by way of illustration with a rod lens relay system or an imaging fiber bundle, to the proximal end so that it can be viewed by means of the eyepiece.

Furthermore, the viewing optic 3 is designed in such a manner that the center region of the distal opening 1' of the tube 1 can be focused; the focus plane of the viewing optic 3 is adjustable. An adjustment ring 34 serves for focusing.

The drawing shows the rod-shaped component 31 of the endoscope serving as the viewing optic 3, which is also disposed outside the tube axis 11 and forms an angle < > ° with it.

Furthermore, the flange 8 is provided with a channel 10 for insertion of another instrument. As both the illumination device 2 and the viewing optic 3 are disposed in the proximal region 1" of tube 1 outside the axis of the tube.

In the preceding the present invention has been described using a preferred embodiment without the intention of limiting the overall inventive concept as, in particular, is set forth in the claims. Of course there are a variety of different modifications possible within this overall inventive concept:

Thus, in particular, the illumination device and the viewing optic can be combined to a unit as is generally usual in endoscopes in which both the illumination light conductor and the relay lens system run in one and the same tube.

What is claimed is:

1. A rectoscope for examination of a body comprising:
    a wide-lumen tube (1) having a distal opening (1') which can be inserted into the body;
    a light conductor connection (6) for transmitting light into said wide-lumen tube (1);
    a viewing optic (3) which can be focused on a center region of the distal opening (1') of said wide-lumen tube (1); and
    substantially an entire internal side of said wide-lumen tube (1) having a semi-reflecting surface such that said internal side of said tube conducts light from said light conductor connection toward the distal opening (1').

2. A rectoscope according to claim 1, characterized by the fact that a focus plane of said viewing optic (3) is adjustable.

3. A rectoscope according to claim 1, characterized by the fact that said viewing optic is an endoscope having a rod-shaped component (31) which only partly projects into the wide-lumen tube (1).

4. A rectoscope according to claim 3, characterized by the fact that said endoscope has an eyepiece (32) which forms an angle < > ° with the rod-shaped component (31) which is inserted into said wide-lumen tube (1).

5. A rectoscope according to claim 3, characterized by the fact that a lens of said endoscope is located in a proximal region (1") of said wide-lumen tube (1).

6. A rectoscope according to claim 1, characterized by the fact that said viewing optic (3) is disposed eccentric in relation to said wide-lumen tube (1).

7. A rectoscope according to claim 1, characterized by the fact that a flange (8) is provided which can be connected to said wide-lumen tube (1) by means of a coupling (5) and to which said viewing optic (3) is attached.

8. A rectoscope according to claim 7, characterized by the fact that said viewing optic (3) is connected to said flange (8) by means of a standard endoscope coupling (9).

9. A rectoscope according to claim 7, characterized by the fact that said flange (8) is provided with at least one channel (10) for the insertion of an additional instrument.

10. A rectoscope according to claim 1, characterized by the fact that a light exit area (71) of said light conductor connection (6) is disposed in a proximal region (1") of said wide-lumen tube (1).

11. A rectoscope according to claim 10, characterized by the fact that said light exit area (71) is not disposed on an axis (11) of said tube (1).

12. A rectoscope according to claim 1, characterized by the fact that axes of said light conductor connection (6) and of said viewing optic (3) form an angle < > °.

* * * * *